Figure 1:
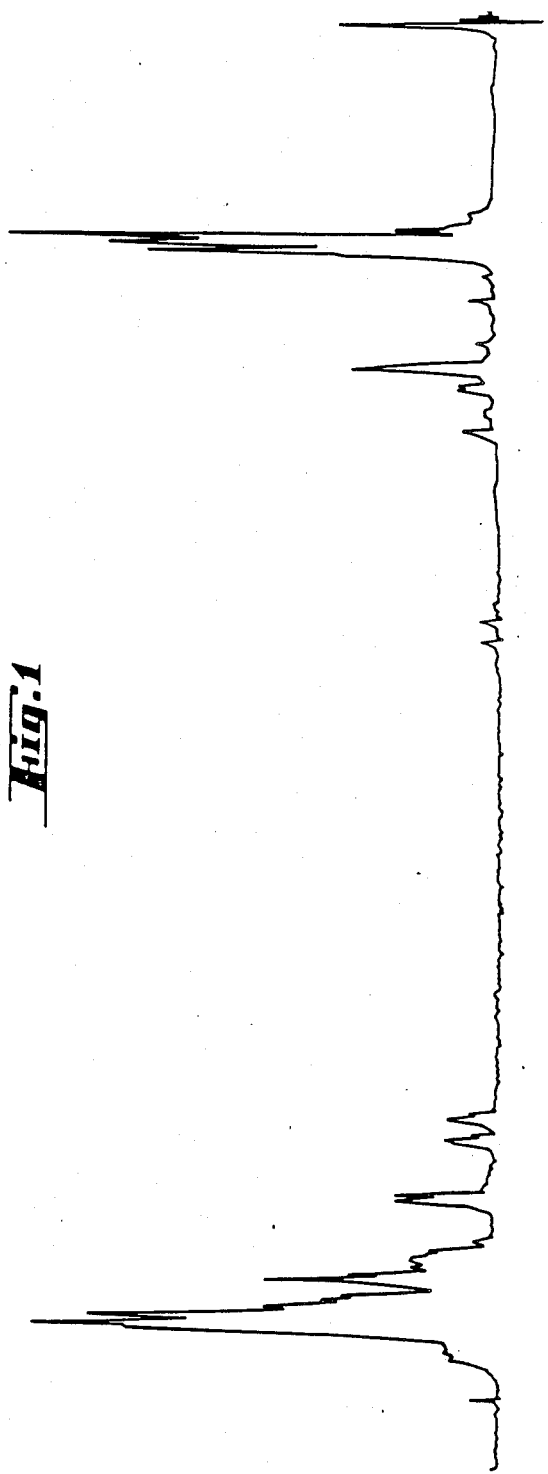

United States Patent [19]

Farooq et al.

[11] Patent Number: 4,681,593
[45] Date of Patent: Jul. 21, 1987

[54] PROCESS AND COMPOSITIONS FOR PROTECTING KERATINOUS MATERIAL FROM ATTACK BY PESTS THAT FEED ON KERATIN, AND NOVEL ESTERS

[75] Inventors: Saleem Farooq, Arisdorf, Switzerland; Dieter Reinehr, Kandern, Fed. Rep. of Germany; Werner Schmid, Riehen, Switzerland

[73] Assignee: Ciba-Geigy Corporation, Ardsley, N.Y.

[21] Appl. No.: 816,462

[22] Filed: Jan. 6, 1986

[30] Foreign Application Priority Data

Jan. 14, 1985 [CH] Switzerland ............... 150/85

[51] Int. Cl.⁴ .................. D06M 3/02; C07C 69/74
[52] U.S. Cl. ..................... 8/128 R; 8/127.5; 560/124
[58] Field of Search ............ 8/127.5, 128 R; 560/124

[56] References Cited

U.S. PATENT DOCUMENTS

| | | | |
|---|---|---|---|
| 3,927,068 | 12/1975 | Searle et al. | 514/937 |
| 3,979,424 | 9/1976 | Searle et al. | 514/937 |
| 3,993,774 | 11/1976 | Searle et al. | 514/531 |
| 4,012,522 | 3/1977 | Searle et al. | 514/531 |

FOREIGN PATENT DOCUMENTS 1413491 5/1973 United Kingdom .

*Primary Examiner*—Paul Lieberman
*Assistant Examiner*—John F. McNally
*Attorney, Agent, or Firm*—Edward McC. Roberts

[57] ABSTRACT

The present invention relates to a process for protecting keratinous material by treating it with an ester of the formula

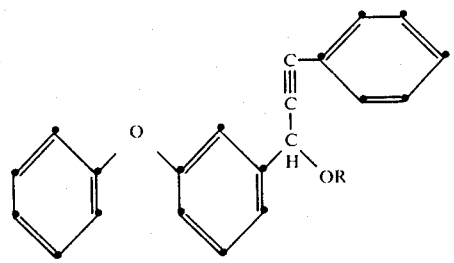

wherein R is the radical of an acid of the formula

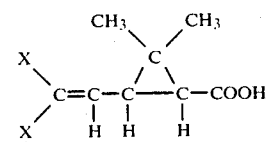

in which X is a $C_1-C_4$ alkyl group or halogen or one of the two substituents X is a phenyl group, or R is the radical of 4-chlorophenylisopropylacetic acid, to compositions containing one or more of these esters, and to novel esters of the formula

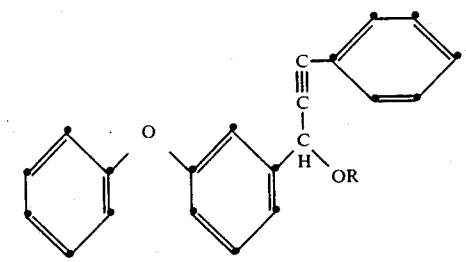

wherein R is the radical of an acid of the formula

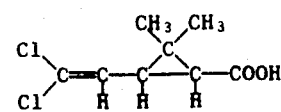

or of 4-chlorophenylisopropylacetic acid.

8 Claims, 2 Drawing Figures

PROCESS AND COMPOSITIONS FOR PROTECTING KERATINOUS MATERIAL FROM ATTACK BY PESTS THAT FEED ON KERATIN, AND NOVEL ESTERS

Esters of the formula

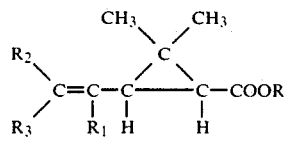

wherein $R_1$ is hydrogen or a methyl group, $R_2$ is hydrogen, halogen or an alkyl group and $R_3$ is hydrogen, halogen or a carbalkoxy group, and R may be the radical of different alcohols, including the 3-phenoxybenzyl radical, are described in GB patent specification No. 1 413 491 of the National Research Development Corporation. The esters of formula (1) are pyrethroids which have pronounced insecticidal properties. Of these pyrethroids, the best known insecticide is Permethrin of the formula

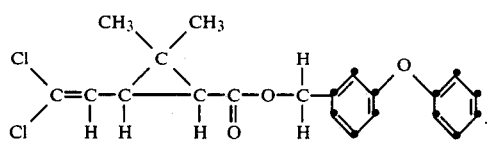

It has now been found that the insecticidal activity of particular esters of formula (1) wherein R is the radical of a 3-phenoxybenzyl alcohol can be increased considerably if, in place of hydrogen, a phenylethynyl group is attached to the methylene group of the alcohol. Such compounds are very suitable for controlling pests in crops of cultivated plants, in particular in crops of rice, while being well tolerated by plants and having low toxicity to warmblooded animals. However, these compounds are suitable in particular for controlling beetles that feed on keratin, as well as the larvae of such beetles, especially the larvae of the carpet beetle. These compounds are therefore suitable for proofing keratinous material against attack by insects that feed on keratin.

Accordingly, the present invention relates to a process for providing keratinous material with a protective finish against attack by insects that feed on keratin, which process comprises treating the material to be protected with an ester of the formula

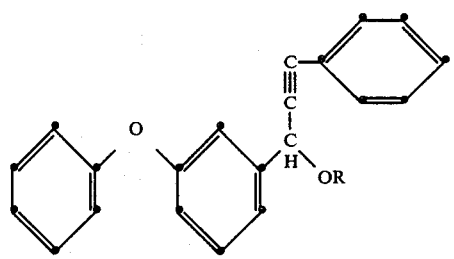

wherein R is the radical of an acid of the formula

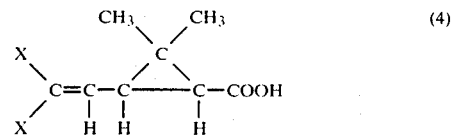

in which X is a $C_1$-$C_4$ alkyl group or halogen or one of the two substituents X is a phenyl group, or R is the radical of 4-chlorophenylisopropylacetic acid.

The material to be protected is preferably treated with an ester of the formula

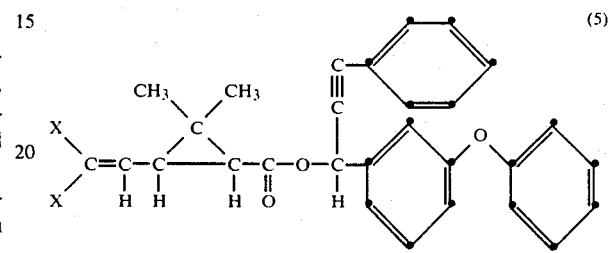

wherein X is a methyl group, chlorine or bromine, and, most preferably, with the ester of the formula

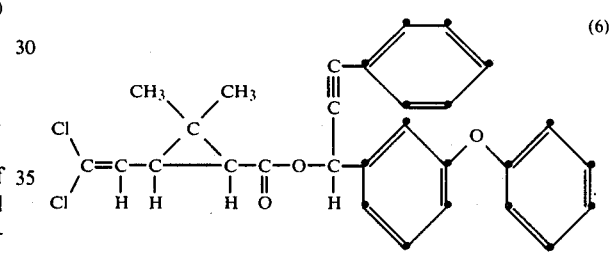

The ester of formula (3) wherein R is the radical of 4-chlorophenylisopropylacetic acid and the ester of formula (6) are hitherto unknown and therefore novel compounds, whereas compounds of formula (5) wherein X is a methyl group or bromine are known from Pesticide Science, 1982, pp. 407–414.

The esters of formula (3) can be prepared by reacting a halide, preferably the cloride, of 4-chlorophenylisopropylacetic acid or of the acid of formula (4) with 3-phenoxy-α-phenylethynylbenzyl alcohol. The alcohol to be employed in the reaction can be obtained by reacting 3-phenoxybenzaldehyde with phenylethynyl magnesium bromide.

The esters to be employed for protecting keratinous material against insects that feed on keratin are effective e.g. against Lepidoptera larvae such as Tineola spec. and Tiena spec., and also Coleoptera larvae, e.g. Anthrenus spec., and Attagenus spec. The esters are most suitable for proofing keratinous material against feeding damage by insects, especially for providing such material with a washfast and lightfast protective finish against insects, in particular moths and beetles. The keratinous material to be proofed can be both in the raw and in the processed state, for example raw or processed sheep's wool or products made of other animal hairs, skins, furs and feathers.

A particularly important feature is the effectiveness of the compounds of formula (3) against the larvae of the webbing clothes moth (*Tineola bisselliella*), the common clothes moth (*Tiena pellionella*) and of the false clothes moth (*Hofmannophila pseudopretella*), as well as against the larvae of fur beetles and carpet beetles (Attagenus spec. and Anthrenus spec. respectively), e.g. against larvae of *Anthrenus verbasci*, of *Anthrenus pimpinellae*, of *Anthrenus scrophulariae*, of *Attangenus pellio* and, in particular, of the black fur beetle (*Attagenus piceus*) and of the carpet beetle (*Anthrenus flavipes*).

The following Examples illustrate that the protective activity against beetles, especially against the larvae of carpet beetles, is better than that achieved with Permethrin:

| Carpet beetle: Anthrenus flavipes; loss of weight in mg[1] | | |
| --- | --- | --- |
| (1) Application by the pad process | | |
| ppm AS[2] applied | Ester Example 1 | Permethrin |
| 30 | 33.4 | 129.5 |
| 60 | 11.9 | 92.8 |
| 125 | 6.5 | 47.8 |
| 250 | 1.5 | 4.1 |
| (2) Application by the dyeing process | | |
| % AS[2] applied | Ester Example 1 | Permethrin |
| 0.0125 | 4.7 | 75.1 |
| 0.025 | 2.6 | 28.8 |
| 0.050 | 0.7 | 2.7 |
| 0.10 | 0.3 | 0.5 |

[1]Biological test according to the Swiss Standards Association (SNV 195'901 - 1971)
[2]Active substance The process of the present invention is therefore preferably used on the one hand for protecting woollen textiles, for example blankets, wool carpets, woollen underwear, woollen clothing, knits and wool-containing textiles such as blends, one component of which is wool, for example blends of wool and other natural fibres, preferably cotton, or of wool and synthetic fibres, and, on the other hand, also for protecting furs and skins from attack by the above-mentioned pests.

The compounds of formula (3) are applied to the above substrates, in particular to woollen textiles and wool-containing textiles, preferably by processes commonly known and employed in dyeing, such as the exhaust process and padding. To this end, an aqueous solution or dispersion (or emulsion or suspension) of the respective active substance is formulated. The active substance can be dissolved beforehand in an organic solvent, such as an aliphatic or alicyclic alcohol, a ketone, a hydrocarbon, such as benzene, a xylene, toluene, a petroleum distillate, and also a chlorinated or fluorinated hydrocarbon, especially in propylene glycol, methoxyethanol, ethoxyethanol or dimethylformamide, and then added to the treatment bath, which can contain additional assistants conventionally used in dyeing, for example dispersants, wetting agents, acids, bases and/or dyes. The organic stock formulation can already contain such assistants.

The textile materials can be impregnated e.g. with hot or cold aqueous dye, bleaching, chroming or aftertreatment baths containing the active ingredients. Various textile finishing processes are possible, for example the pad or exhaust process.

The treatment is conveniently carried out in the temperature range from 10° to 100° C., in the dye bath preferably in the range from about 60° to 100° C. and in the aftertreatment or wash bath preferably in the range from 10° to 70° C, preferably from 20° to 60° C.

As further assistants there may be added to the treatment baths e.g. dispersants, emulsifiers or surfactants.

The liquor can additionally contain further conventional assistants, such as water-soluble perborates, polyphosphates, carbonates, silicates, fluorescent whitening agents, softeners, salts with acid reaction, such as ammonium or zinc silicofluoride, or certain organic acids such as oxalic acid, acetic acid or, in particular, formic acid, and also antimicrobial agents and finishing agents, for example those based on synthetic resins or starch. If the mothproof and beetle-resistant finishing is carried out together with the dyeing of the material (e.g. wool), the baths additionally contain the corresponding dyes and, if appropriate, the necessary assistants, e.g. levelling agents.

The aqueous treatment baths contain, for example, surfactants, for example anionic compounds, such as soaps and other carboxylates (e.g. alkali metal salts of higher fatty acids), derivatives of sulfur oxyacids (e.g. the sodium salt of dodecylbenzenesulfonic acid, water-soluble salts of sulfuric acid monoesters of higher molecular alcohols or of their polyglycol ethers, for example soluble salts of dodecyl alcohol sulfate or of dodecyl alcohol polyglycol ether sulfate), derivatives of phosphorus oxyacids (e.g. phosphates), derivatives with acid (electrophilic) nitrogen in the hydrophilic group (e.g. disulfine salts), cationic surface-active agents, such as amines and their salts (e.g. lauryldiethylenetriamine), onium compounds, amine oxides or nonionic surface-active agents, such as polyhydroxy compounds, surface-active agents based on mono-or polysaccharides, higher molecular acetylene glycols, polyglycol ethers (e.g. polyglycol ethers of higher fatty alcohols, polyglycol ethers of higher molecular alkylated phenols).

If non-aqueous application is made (solvent application), an appropriate amount of a compound of formula (3) may also be added to a suitable solvent and the material to be protected may be impregnated with the solution so obtained. Suitable solvents for this application are, inter alia, trichloroethylene, methylene chloride, hydrocarbons, propylene glycol, methoxyethanol, ethoxyethanol, dimethylformamide, to which dispersants (e.g. emulsifiers, such as sulfated castor oil, fatty alcohol sulfates etc) and/or other assistants can be added. The material to be protected is usually simply impregnated with these solutions.

The proofing of the material to be protected may also be combined with a dry cleaning process. To this end, an appropriate amount of a compound of formula (3) is dissolved in the cleansing agent (such as a lower halogenated alkane, e.g. trichloroethylene etc.) and the cleaning process is carried out in the usual manner.

However, an amount of a compound of formula (3) may also be dissolved in a readily volatile organic solvent and the resultant solution then sprayed onto the substrate to be protected (spray application). Textile fabrics which contain wool, furs and feathers are particularly suitable for this application. The advantage of the spray application is that pollution of the wastewaters is avoided on account of the recovery of the solvent.

In the process of the present invention, the compounds of formula (3) may also be used in combination with other protectants which act against insects that feed on keratin, for example with urea derivatives, benzimidazoles, aromatic sulfonamides and phosphoric and phosphonic acid esters and 5-phenylcarbamoylbarbituric acid derivatives.

The amount of compound of formula (3) which is added to the treatment bath or non-aqueous solvent depends on the substrate and the method of application.

However, this amount is ordinarily such that, after application to the material which it is desired to protect, the latter contains about 10 to 2000 ppm, preferably 100 to 1000 ppm, of compound of formula (3) with the upper limit being largely determined by economic considerations, whereas the lower limit depends on criteria such as the intended breadth and permanency of the protective action. This corresponds, for example, to concentrations of 0.001 to 1 g of active ingredient per liter of treatment bath using the exhaust process at a liquor to goods ratio of 1:20, depending on the degree of exhaustion attainable. In the pad process concentrations of up to 2 g of active ingredient per liter are possible.

Finally, the present invention also relates to compositions for providing keratinous material with a protective finish against attack by pests that feed on keratin, which compositions contain the novel esters of formula (3). The compositions of the present invention may, in addition to the active ingredient, contain conventional carriers and/or formulation assistants, e.g. organic solvents, water, acids, bases, wetting agents, dispersants and/or emulsifiers. The compositions of this invention may also contain assistants which are described above as assistants in the treatment bath for the proofing process of this invention. Further, the compositions of the present invention may also contain other protectants which act against insects that feed on keratin, e.g. urea derivatives, benzimidazoles, aromatic sulfonamieds, phosphoric and phosphonic acid esters and/or 5-phenylcarbamoylbarbituric acid derivatives.

The preparation of 3-phenoxy-α-(2-phenyethynyl)-benzyl 2,2-dimethyl-3-(2,2-dichlorovinyl)cyclopropanecarboxylate as well as of the starting 3-phenoxy-α-phenylethynylbenzyl alcohol is described in the following Examples:

EXAMPLE 1

While cooling with ice and with exlusion of air ($N_2$ flushing), 1.8 ml of pyridine followed by a solution of 6 g of 3-phenoxy-α-phenylethynylbenzyl alcohol in 20 ml of toluene are added dropwise to a solution of 4.51 g of 2,2-dimethyl-3-(2,2-dichlorovinyl)cyclopropylcarboxylic acid chloride in 50 ml of toluene. The reaction mixture is stirred overnight and then diluted with about 200 ml of toluene and about 200 ml of water, extracted in succession with 2n HCl, 10% $K_2CO_3$, 10% $NaHCO_3$ and a saturated solution of NaCl, dried over $Na_2SO_4$ and concentrated by rotary evaporation. The concentrated solution is filtered over 200 g of silica gel and eluted with a 95:5 mixture of hexane and ether. The solvent is removed, affording 8.0 g of 3-phenoxy-α-(2-phenylethynyl)benzyl-2,2-dimethyl-3-(2,2-dichlorovinyl)cyclopropanecarboxylate of the formula

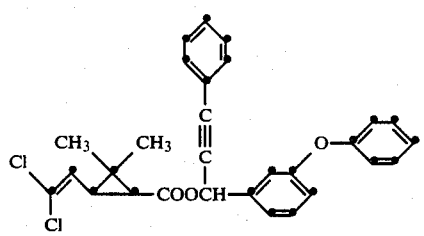

in the form of a pale yellow oil with a refractive index of $n_D^{20} = 1.5943$ and with an NMR spectrum as shown in FIG. 1. The yield is 81.8 % of theory.

EXAMPLE 2

The alcohol required for the preparation of the pyrethroid is prepared as follows:

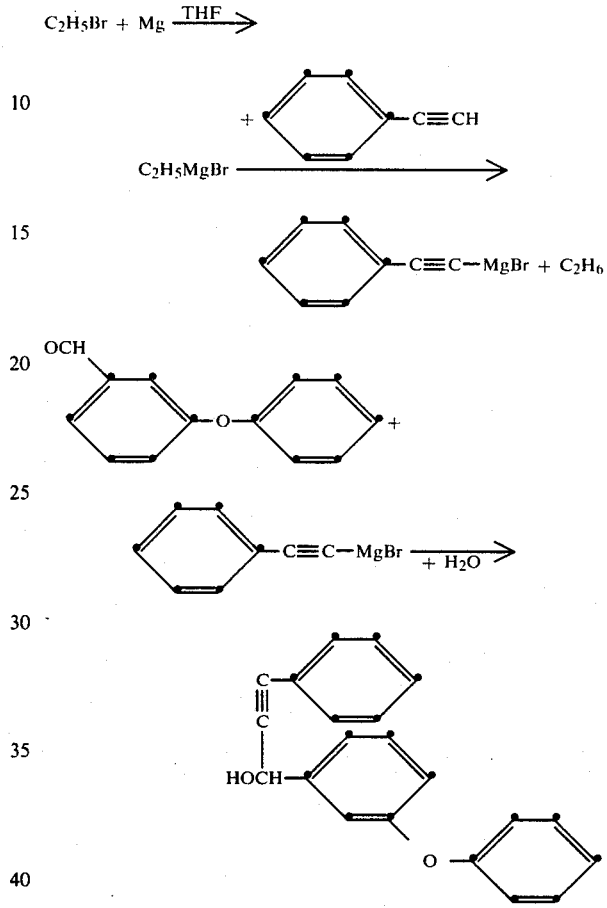

THF = tetrahydrofuran

Figure 2:
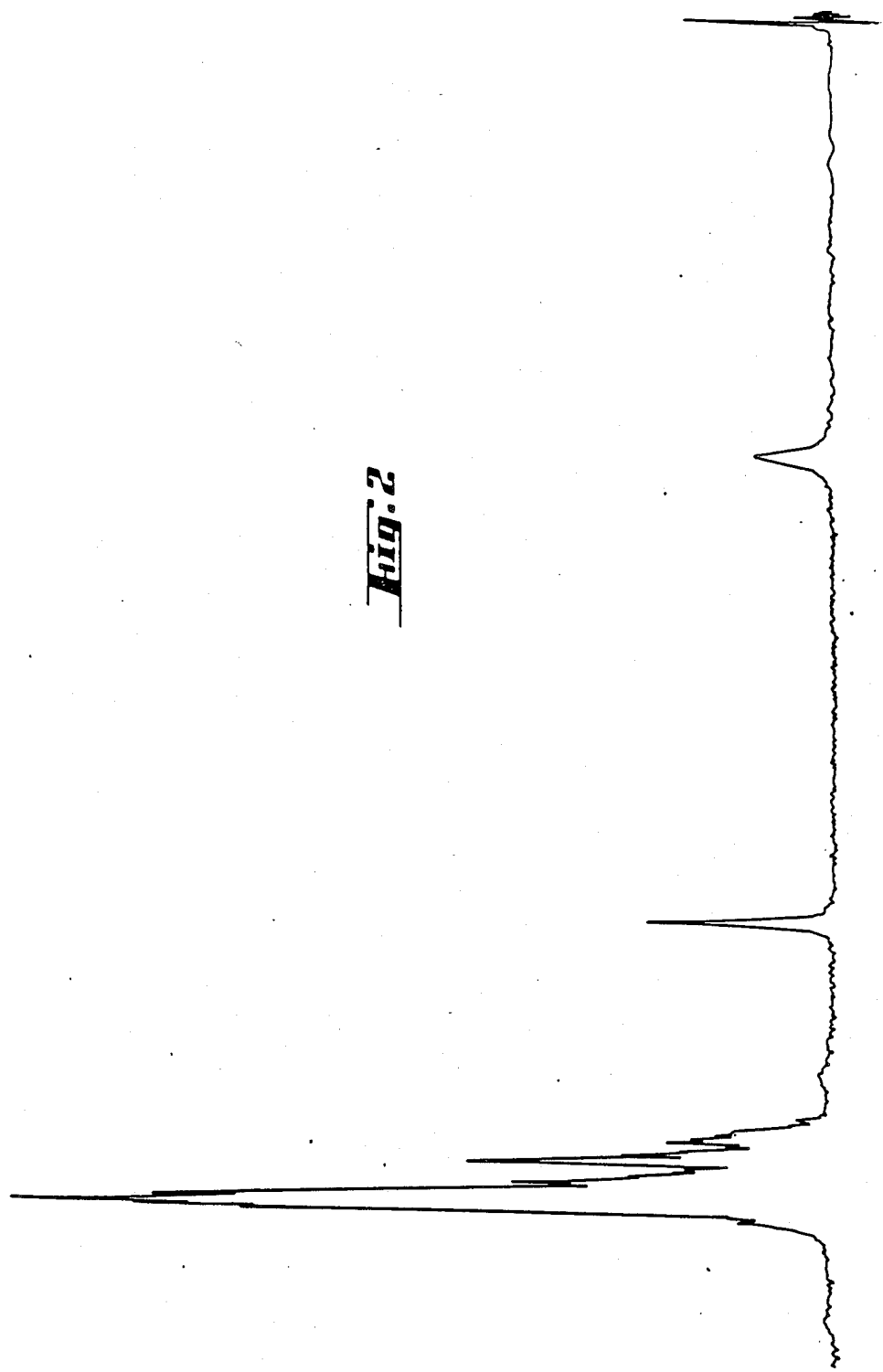

A reaction vessel is charged with 14.6 g of magnesium filings together with a trace of iodine crystals. 73.6 g of ethyl bromide in 25 ml of tetrahydrofuran are then added dropwise such that the tetrahydrofuran boils gently under reflux. The Grignard solution formed is added dropwise at 0°–5° C. to a solution of 62.1 g of phenylacetylene in 250 ml of tetrahydrofuran and the mixture is stirred until the evolution of gas ceases. The resultant solution is cooled to 0° C. and 99 g of 3-phenoxybenzaldehyde are added dropwise such that the temperature does no exceed +5° C. The reaction mixture is stirred overnight at room temperature and then cooled to a temperature in the range from 0° to +5° C. About 100 g of ice are added, whereupon a precipitate forms which is dissolved in 100 ml of concentrated HCl. The aqueous solution is extracted with three 150 ml portions of ether and the extracts are washed with $NaHCO_3$ solution and then dried over $Na_2SO_4$. The ether is distilled off by rotary evaporation, affording as residue 148 g of 3-phenoxy-α-phenylethynylbenzyl alcohol with a refractive index of $n_D^{23} = 1.6238$ and with an NMR spectrum as shown in FIG. 2. The yield is 98.8 % of theory.

FIGS. 1 and 2 show the NMR spectra of the compounds of Examples 1, and 2, respectively.

What is claimed is:

1. A process for providing keratinous material with a protective finish against attack by insects that feed on keratin, which process comprises treating the material to be protected with an ester of the formula

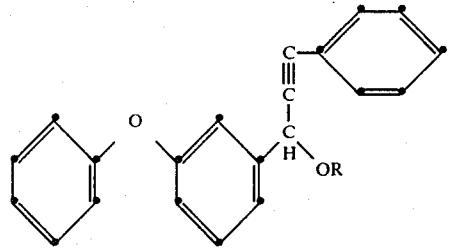

wherein R is the radical of an acid of the formula

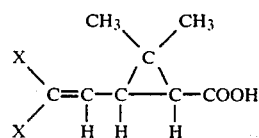

in which X is a $C_1$–$C_4$ alkyl group or halogen or one of the two substituents X is a phenyl group, or R is the radical of 4-chlorophenylisopropylacetic acid.

2. A process according to claim 1, which comprises treating the material to be protected with an ester of the formula

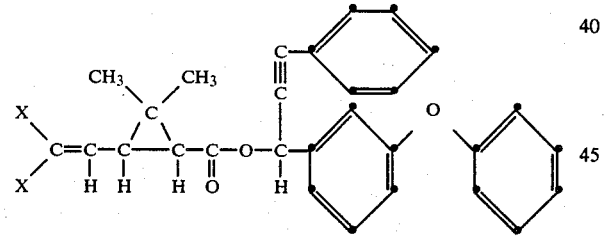

wherein X is a methyl group, chlorine or bromine.

3. A process according to claim 1, which comprises treating the material to be protected with an ester of the formula

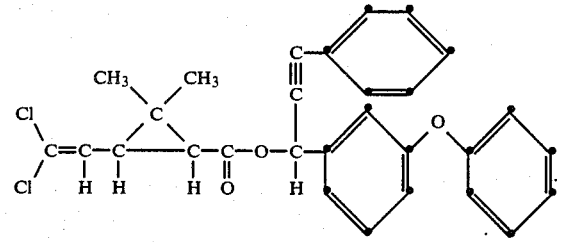

4. An ester of the formula

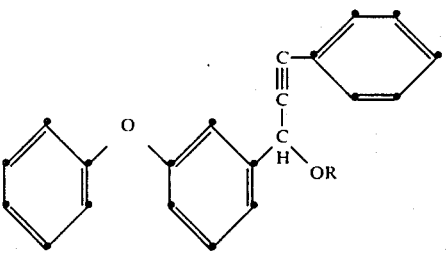

wherein R is the radical of an acid of the formula

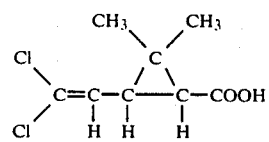

or of 4-chlorophenylisopropylacetic acid.

5. An ester according to claim 4 of the formula

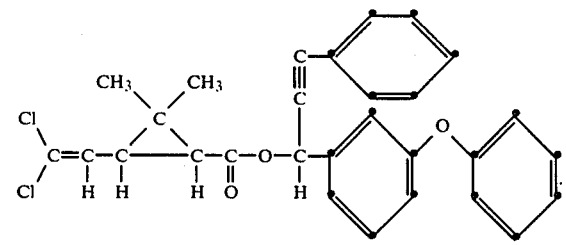

6. An ester according to claim 4 of the formula

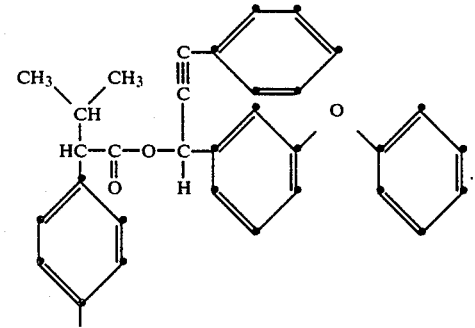

7. A composition for providing keratinous material with a protective finish against attack by pests that feed on keratin, which composition contains one or more esters of the formula

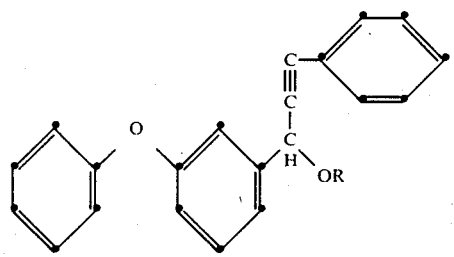
wherein R is the radical of an acid of the formula
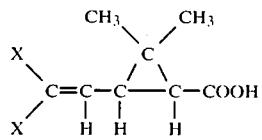
in which X is a $C_1$-$C_4$alkyl group or halogen or one of the two substituents X is a phenyl group, or R is the radical of 4-chlorophenylisopropylacetic acid.
8. The keratinous material treated by the process according to claim 1.
* * * * *